United States Patent [19]

Bésán et al.

[11] Patent Number: 4,490,539

[45] Date of Patent: Dec. 25, 1984

[54] PROCESS FOR THE PREPARATION OF 1,2,4-TRIAZOLE

[75] Inventors: János Bésán; Miklós Kovacs; László Kulcsár; Ferenc Maier; József Pernyeszi, all of Veszprem, Hungary

[73] Assignee: Nehezvegyipari Kutato Intezet, Veszprem, Hungary

[21] Appl. No.: 390,863

[22] Filed: Jun. 22, 1982

[51] Int. Cl.³ ............................................. C07D 249/08
[52] U.S. Cl. ............................................................ 548/262
[58] Field of Search ............................................... 548/262

[56] References Cited

U.S. PATENT DOCUMENTS

| | | | |
|---|---|---|---|
| 4,267,346 | 5/1981 | Kaiser et al. | 548/262 |
| 4,267,347 | 5/1981 | Petree et al. | 548/262 |
| 4,283,545 | 8/1981 | Knorr et al. | 548/262 |
| 4,390,704 | 6/1983 | Beer | 548/262 |

OTHER PUBLICATIONS

Ainsworth et al., J. Am. Chem. Soc., vol. 77, pp. 621-624 (1955).

Primary Examiner—Alton D. Rollins
Attorney, Agent, or Firm—Young & Thompson

[57] ABSTRACT

A process for the preparation of 1,2,4-triazole by reacting hydrazine, formic acid and formamide and/or ammonia in a molar ratio of 1 mole of hydrazine to 1 to 3 moles of formic acid to 1 to 2 moles of formamide and/or ammonia at a temperature of 140° to 220° C. The main advantage of the process of the invention resides in obtaining 1,2,4-triazole with an improved yield and purity.

7 Claims, No Drawings

PROCESS FOR THE PREPARATION OF 1,2,4-TRIAZOLE

FIELD OF THE INVENTION

The present invention relates to a novel process for the preparation of 1,2,4-triazole by reacting hydrazine, formic acid as well as formamide and/or ammonia.

BACKGROUND OF THE INVENTION 1,2,4-triazole is mainly used in the production of plant protection agents and by the pharmaceutical industry.

For the preparation of 1,2,4-triazole many processes are known. Of these processes those are now disclosed which are closest to the present invention.

According to the Luxemburgian patent specification No. 61,617 1,2,4-triazole can be prepared by reacting 1 mole of hydrazine and 3 moles of formamide at a temperature of 90° to 260° C. in accordance with equations 1 and 2.

$$H_2N-NH_2 + 2H-CO-NH_2 \longrightarrow \quad (1)$$

$$H-CO-NH-NH-CO-H + 2NH_3$$

$$(I)$$

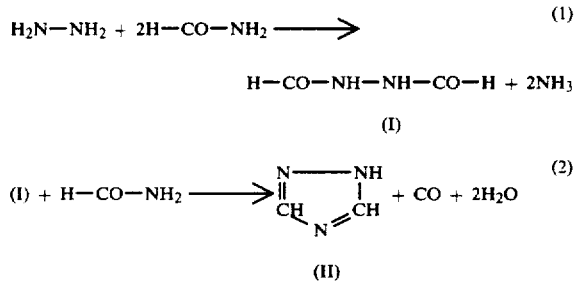 (2)

(II)

The main disadvantage of this process is the high demand on formamide. At the same time a great part of the ammonia contents of formamide gets lost as waste and therefore the industrial realization of this process is uneconomical.

The German patent specification No. 2,802,491 discloses also a process starting from these two reagents and further from ammonia. According to this process the reaction is carried out at a temperature of 100° to 250° C., preferably at 110° to 220° C., in an apparatus comprising 3 or 4 reactors in series while the gases and vapours are condensed at different temperatures and the condensates as well as the gases and vapours are recycled into one or another reactor. In this process instead of 3 moles of formamide (3−n) moles of formamide are used where $0.3 \leq n \leq 1$, that is, the formamide is partly substituted by ammonia—c.f. equation 3.

$$H_2N-NH_2+(3-n)H-CO-NH_2+nNH_3 \rightarrow (II)+2H_2O++2NH_3+(1-n)CO \quad (3)$$

$$0.3 \leq n \leq 1$$

This process is very complicated in view of the necessity of ensuring the balance of the cascade system, further of the cooling of the gaseous and vaporous products to different temperatures and the distribution of the condensates as well as of the gases, at the same time the reduction of the consumption of formamide is not significant.

The triazole ring can also be formed via diformylhydrazine (C. Ainsworth and R. B. Jones: J. Am. Chem. Soc. 1955. 77, p. 621-24). Diformylhydrazine was prepared from formic acid and hydrazine according to equation 4 by heating for 12 hours at a temperature of 100° C. with a yield of altogether 60%.

$$H_2N-NH_2+2H-COOH \rightarrow (I)+2H_2O \quad (4)$$

Diformylhydrazine can be also obtained from hydrazine and formamide at a temperature of 100° C. within 2 hours; the yield is, however, only 80% (c.f. equation 1). The ring closure of diformylhydrazine to 1,2,4-triazole can be carried out with ammonia according to equation 5, namely with condensed ammonia, by heating the reaction mixture under pressure at a temperature of 200° C. for 24 hours.

$$(I)+NH_3 \rightarrow (II)+2H_2O \quad (5)$$

1,2,4-Triazole is formed with a yield of 70 to 80%. The total yield, based on hydrazine, is in both cases less than 60%. These processes are difficult and uneconomical.

Thus, for the ring closure of diformylhydrazine formamide, ammonia or formamide and ammonia, respectively, are used (c.f. equations 2 and 3). Besides the main reaction, however, numerous side reactions can take place, e.g. the reactions represented by equations 6, 7 and 8, see on the next page [A. Étienne: Traité de chimie organique (V. Grignara et al. editor) 21, 898, Masson, Paris 1953; A. Hetzheim and K. Möckel: Advan.-Heterocyclic Chem. 7, 183-224 (1966); G. H. Schwab: Z.anorg. allg. Chem. 262, 41-8 (1950)].

OBJECT OF THE INVENTION

The aim of the present invention is the elaboration of a process by which 1,2-triazole can be prepared in an easier and cheaper way than before.

SUMMARY OF THE INVENTION

When studying the reaction of hydrazine, formic acid, formamide and/or ammonia the surprising recognition was made that under certain conditions the salt of formic acid formed with hydrazine, i.e. hydrazine-formite, or the hydrazine itself is capable of ring closure with formamide or with a mixture of formic acid and/or ammonia without preparing diformylhydrazine previously. This surprising recognition has not been known up to now and could not have been expected either. The reaction of hydrazine, formic acid as well as of formamide and/or ammonia leads to the formation of 1,2,4-triazole with high speed and very good yield without the formation of 4-amino-1,2,4-triazole and 1,3,4-oxadiazole impurities, respectively, in the side reactions represented by equations 6 and 7.

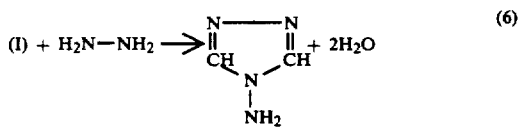 (6)

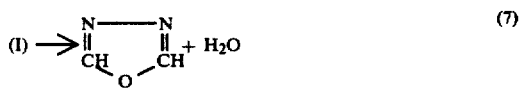 (7)

$$H-CO-NH_2 \rightarrow CO + NH_3 \quad (8)$$

The process of the invention is described by gross reaction equation 9.

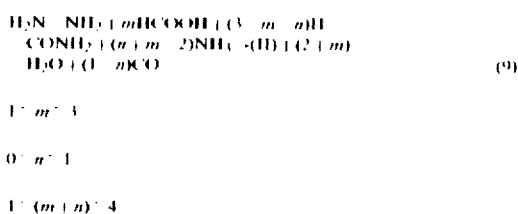

$1 \leq m \leq 3$ $0 \leq n \leq 1$ $1 \leq (m+n) \leq 4$

The quick and complete reaction of hydrazine, formic acid as well as of formamide and/or ammonia can be attained so that hydrazine or hydrazine and formic acid are reacted at a temperature of about 180° C. with formamide or a mixture of ammonia and formic acid. In the course of this reaction step it is advantageous if the reaction mixture is saturated with ammonia. This can be realized by introducing gaseous ammonia into the reaction mixture or by saturating the solution of hydrazine or hydrazine-formiate in water, formamide or a mixture of water and formamide with ammonia gas or by admixing it with a solution of ammonia. The quantity of formamide converted during the reaction can be partly or completely supplemented by ammonia. Under such conditions the formation of 1,2,4-triazole is so rapid that the rate of the feeding is determined by the speed of the heat transfer. Important is that the temperature of the reaction mixture can not drop under 140° C. and rise above 220° C. because in the former case the reaction slows down, while in the latter case the distillation loss becomes significant. After finishing the feeding of hydrazine-formiate or hydrazine into formamide or a mixture of formic acid and ammonia the reaction mixture is still kept at 180° C. for 10 minutes, then it is cooled. Depending on the composition and the ratio of the reactants the bulk of the formed 1,2,4-triazole crystallizes or the reaction mixture hardens. In both cases the yield is about 95%.

The molar ratio of hydrazine to formic acid is about 1:1 to 3, while the quantity of formamide and/or ammonia, based on 1 mole of hydrazine, is 1 to 2 moles.

In the course of the reactor one must ensure that after condensation the escaping water vapour should not get back into the system.

The reaction product is a pure, colourless, homogeneous liquid, at the cooling of which the formed 1,2,4-triazole separates as a white crystalline substance, or the whole hardens to a white crystalline mass.

The reaction time for the formation of 1,2,4-triazole is about 5 to 60 minutes, depending on the reaction temperature, further on the molar ratio and the composition of the reactants. The reaction temperature is between 140° and 220° C., preferably at about 180° C.

A possible way of performing the process of the invention is the use of formamide in excess. Its role is twofold, on the one hand it is a solvent and optionally increases the solubility of ammonia, on the other hand it ensures that during the feeding of the reactants a small quantity of hydrazine or hydrazine-formiate always contacts formamide being in a high excess. In this case about 6 percent by weight of 1,2,4-triazole remain dissolved in the excess of formamide after the filtration of the crystalline product. The filtrate can be used repeatedly by recycling.

In the course of the process of the invention the recovery of the formamide remaining in the distilled water can be carried out simultaneously with the reaction or after collection from time to time, and the thus recovered formamide can be recycled.

Another possibility of performing the process of the invention is to use hydrazine, formic acid and ammonia for the reaction, when doing so a mixture of hydrazine-formiate and ammonia is added preferably to a solution of ammonium formiate at a temperature of 180° C. The appropriate speed of the formation of 1,2,4-triazole is ensured by ammonia excess in the reaction mixture. The product is a substance consisting of white crystals with a melting point of 98° to 102° C. when the reaction temperature is 180° C.

It is advantageous to transfer the mixture leaving the reaction vessel and containing water vapour, ammonia, some starting substance, intermediate reaction products and the formed 1,2,4-triazole into a condenser at a temperature of 110°-140° C., from where the still useful components are returned as condensates into the reaction mixture. The water vapour and ammonia leaving the condenser are then cooled to 20° to 80° C. and the ammonia is partly or entirely recycled into the reaction mixture; thus it is ensured that the reaction mixture is always saturated with ammonia. The ammonia added in an excess can be absorbed in formic acid and again recycled into the preparation process.

If after carrying out the reaction some water and formamide being in the obtained product are to be removed, this can be attained by distillation carried out in vacuo at a temperature of 160° C. or, alternatively, by keeping the product at a temperature of 210° to 230° C. The vapours formed during these steps can be used again in the preparation process after condensation.

The process of the invention can be performed either batch-wise or continuously.

The present process is illustrated by the following non-limiting examples.

EXAMPLE 1

Into a round-bottom flask with a volume of 250 ml 92 g. (2.0 moles) of formic acid are introduced and within 10 minutes 69.5 g. (1.0 moles) of 72% hydrazine hydrate solution are added. Meanwhile, the cooling is controlled so that at the end of the feeding the temperature of the reaction mixture should be 80° C. In the meantime into another round-bottom flask with a volume of 250 ml 76.5 g. (1.7 moles) of formamide are introduced and heated to 180° C. To this formamide the hydrazine-formiate solution with a temperature of 80° C. is added at such a rate that the temperature of the reaction mixture should remain between 175°-185° C. In the course of the feeding the water brought in with the hydrazine-hydrate and formed in the reaction is removed via a distillation apparatus connected to the round-bottom flask. After the termination of the feeding of hydrazine-formiate the reaction mixture is kept at a temperature of 180° C. for further 10 minutes, then it is allowed to cool and finally it is cooled to 1° to 2° C. Separated 1,2,4-triazole is recovered by filtration. The mass of the dry product is 60.5 g., while its melting point is 120° to 121° C. The mass of the filtrate 26.5 g. and contains 19.5% of dissolved 1,2,4-triazole; thus the total yield, based on hydrazine, is 95.8%.

EXAMPLE 2

Into a round-bottom flask with a volume of 250 ml 135 g. (2.5 mole) of 85% formic acid are introduced and under cooling 69.5 g. (1.0 moles) of 72% hydrazine hydrate are added. At the same time ammonia is led into the system with a speed of 6 l/h. The temperature of the reaction mixture is kept under 20° C. After finishing the feeding of hydrazine hydrate the introduction of ammonia is continued until saturation. Into another round-bottom flask with a volume of 250 ml 45 g. (1.0 moles) of formamide are introduced and heated to 170° C. The hydrazine-formate solution saturated with ammonia is added to this formamide. The temperature of the formamide is controlled partly by heating, partly by the feeding speed so that it is steadily above 160° C. The water brought in with the reagents and formed in the reaction is removed with the help of a distillation apparatus. The feeding takes totally 50 to 55 minutes, then the reaction mixture is kept at said temperature for still 15 minutes, whereafter it is allowed to cool and finally it is cooled to −1° to −2° C. The 1,2,4-triazole separated is filtered and thoroughly sucked off. The mass of the dry product is 58.9 g., while that of the filtrate 35.2 g. The latter contains 19.1% of dissolved 1,2,4-triazole; thus the total yield, based on hydrazine, is 95.1%.

EXAMPLE 3

Into a round-bottom flask with a volume of 250 ml 92 g. (2 moles) of formic acid and 45 g. (1 mole) of formamide are weighed. Within 10 minutes 32. g. (1 mole) of hydrazine are added. The temperature of the reaction mixture is kept at 40° C. Into another flask 22.5 g. of formamide are weighed and heated to 180° C. Under intensive stirring the formamidic solution of the hydrazine-formate is added to it within 1 hour, while ammonia is fed with a speed of 10 l/h. After 10 minutes of post-stirring the feeding of ammonia is stopped, the reaction mixture is cooled to −2° C. and the 1,2,4-triazole is filtrated off. The mass of the dry product is 61.1 g., while that of the filtrate 20.5 g. In the course of the feeding of the hydrazine-formate 75 g. of distillate were collected in the distillation apparatus.

EXAMPLE 4

The reaction is carried out as described in Example 3. After stopping the feeding of ammonia the formamide is distilled off in vacuo at a temperature of 160° C. The 1,2,4-triazole obtained in the form of a melt is solidified. The mass of the thus-obtained 1,2,4-triazole is 64.8 g.

EXAMPLE 5

A 85 percent formic acid and 73 percent hydrazine hydrate are mixed together in a molar ratio of 2:1 under cooling. Into a round-bottom flask provided with an overflow pipe, a distillation apparatus, mixer and thermometer and having a volume of 100 ml 180 g. of the hydrazine-formate prepared according to the above described, further 69 g. of formamide are added per hour. The contents of the flask are kept steadily at a temperature of 180° C. Every hour 75 g. of a 1,2,4-triazole solution leave the flask; from this solution 62.1 g. of dry 1,2,4-trazole can be recovered.

EXAMPLE 6

A cascade system with an overflow pipe provided with a liquid closing was construed from 3 flasks with a volume of 100 ml each. Every flask is provided with a mixer and a thermometer; to the first one a reflux condenser, to the second and third one a distillation apparatus is attached. Into the first flask 85 percent formic acid is fed with a speed of 108 g/h and 72 percent hydrazinehydrate with a speed of 70 g/h. In this flask the temperature of the reaction mixture is kept at 80° C. The reaction mixture gets via said overflow pipe into the second flask kept at a temperature of 180° C., into which formamide is introduced at a speed of 77 g/h. The distillate collected in the distillation apparatus contains some formamide, too, therefore the collected aqueous solution is distilled again and this water-free formamide is fed back into the second flask. The reaction mixture gets into the third flask where—keeping the temperature at 190° C.—the last traces of water are distilled off. The formamidic solution of 1,2,4-triazole leaves the flask with a speed of 95–98 g/h. The 1,2,4-triazole is covered from the reaction mixture by freezing out and filtration, and the mother liquor is recycled back into the second flask. In the system 1,2,4-triazole is formed with a speed of 67.5 g./h and a melting point of 120°–121° C.

EXAMPLE 7

Into a round-bottom flask with a volume of 250 ml 54.2 g. (1.0 mole) of 85 percent formic acid are introduced and 69.4 g. (1.0 mole) of 24.5 percent ammonium hydroxide solution are added. The formed ammonium-formate solution is heated to 180° C. while adding gaseous ammonia steadily and under stirring so that the water brought in with the solutions and formed in the reaction is removed via the distillation apparatus connected to the round-bottom flask. When the temperature of 180° C. is reached the addition of gaseous ammonia is stopped. Meanwhile, hydrazine-formate is prepared from 70.5 g. of 71 percent (1.0 mole) hydrazine hydrate and from 54.2 g. (1.0 mole) of 85 percent formic acid and to this 34.7 g. (0.5 moles) of 24.5 percent ammonium hydroxide solution are added. The thus-obtained reaction mixture is fed into the round-bottom flask under continuous water removal and stirring so that the temperature is between 175° and 185° C. After having fed the hydrazine formate and ammonium hydroxide solution the reaction mixture is kept at a temperature of 180° C. for still 10 minutes. The mass of the cooled white crystalline 1,2,4-triazole is 65.8 g., the yield, based on hydrazine hydrate, 95.3%. The purity of the product is 93%.

EXAMPLE 8

The preparation of 1,2,4-triazole is carried out as described in Example 7 but after the feeding of the hydrazine-formate and the ammonium hydroxide solution the temperature of the reaction mixture is increased to 220° C. and kept at this value for 15 minutes. The mass of the obtained 1,2,4-triazole is 62 g., its purity 97%. The condensate is used in the following preparation process.

EXAMPLE 9

Into a round-bottom flask with the volume of 250 ml 108.4 g. of 85 percent (2.0 moles) formic acid and 138.8 g. of 24.5 percent (2.0 moles) ammonium hydroxide solution are introduced, then one proceeds as in Example 7 with the difference that when reaching the temperature of 180° C. not hydrazine-formate, but the mixture of 70.5 g. of 71 percent (1.0 mole) hydrazine hydrate and 34.7 g. of 24.5 percent (0.5 moles) ammonium hydroxide solution is fed into the round-bottom flask. The mass of the obtained 1,2,4-triazole is 66.0 g..

EXAMPLE 10

Into a round-bottom flask with a volume of 250 ml 86 g. of 100 percent (1.9 moles) formamide are weighed and heated to 180° C., then under continuous stirring and water removal 70.5 g. of 71 percent (1.0 moles) hydrazine hydrate solution and 5.4 g. of 85 percent (0.1 moles) formic acid are added so that the temperature remains between 175° and 185° C. After adding the hydrazine hydrate and the formic acid the reaction mixture is kept at a temperature of 180° C. for still 10 minutes, then one lets it cool. The mass of the solidified crystalline product is 66.0 g., the yield 95.7%.

EXAMPLE 11

In a reactor with a volume of 1000 ml and provided with a mixer, an overflow and distillation apparatus the 1,2,4-triazole solution according to Examples 7,8, 9 or 10 was prepared, then into the melt of a temperature of 180° C. the aqueous solution of hydrazine, formic acid and ammonia is fed with a molar ratio of 1:2:1.3 and a feeding speed of 434 g./h. The gases and vapours leaving the reactor are cooled to 125° C., the condensate is returned into the reaction vessel. The condensate containing ammonia and the water formed in the course of the further cooling of the gases and vapours to 125° C. is withdrawn, the gaseous ammonia is returned into the reaction vessel. The ammonia used in excess is absorbed and again used in the process. The mass of the 1,2,4-triazole leaving at the overflow of the reactor continuously at a temperature of 100° C. is 100.3 g., the yield, based on hydrazine, 96.9% and the purity of the product 92.0%.

EXAMPLE 12

The melt leaving the reactor described in Example 11 is continuously fed into a vessel at a temperature of 220° C. and a volume of 250 ml, said vessel being provided with an overflow, a mixer and a distillation apparatus. The formed vapours are cooled to 60° C., the condensate is returned into the reactor of Example 11. The quantity of 1,2,4-triazole leaving at the overflow is 98.3 g./h, the purity of the product 98.0%.

The present process has the following main advantages:

cheap starting substances available in large quantities are used;

the ring closure is fast and nearly quantitative;

the reagents used in excess can be recycled;

every reaction of the process is fast and proceeds in homogeneous phase, thus the process can be carried out in one step, simply and in continuous operation, too; and the 1,2,4-triazole obtained in crystalline state is very pure.

What we claim is:

1. A process for the preparation of 1,2,4-triazole by reacting hydrazine, formic acid and formamide and/or ammonia characterized in that said hydrazine and formic acid or their aqueous solutions are reacted in the presence of formamide and/or ammonia in a molar ratio of 1 mole of hydrazine to 1 to 3 moles of formic acid to 1 to 2 moles of formamide and/or ammonia at a temperature of 140° to 220° C., the formed 1,2,4-triazole is recovered from the reaction mixture in a known manner and optionally the reagents used in excess are recycled.

2. Process as claimed in claim 1 characterized in that hydrazine, an aqueous or water-free mixture of hydrazine and formic acid or of hydrazine, formic acid and ammonia is added to a water-free or aqueous mixture of ammonia and formic acid.

3. Process as claimed in claim 1 characterized in that the reagents are added into a melt or solution of 1,2,4-triazole.

4. Process as claimed in claim 1 characterized in that the ammonia formed in the course of the reaction is partly or completely recycled.

5. Process as claimed in claim 1 characterized in that the formed water-formamide mixture is separated and the water-free formamide is optionally recycled.

6. Process as claimed in claim 1 characterized in that the formed vapours are cooled to 110°-140° C. and the condensate is returned into the reaction mixture.

7. A process as claimed in claim 1 characterized in that an aqueous or anhydrous mixture of either hydrazine and formic acid, or hydrazine and formic acid and formamide, is added to formamide, optionally in the presence of ammonia.

* * * * *